United States Patent [19]

Nishida et al.

[11] Patent Number: 5,484,933
[45] Date of Patent: Jan. 16, 1996

[54] PROCESS FOR PRODUCTION OF FLUOROALKANE CARBOXAMIDE DERIVATIVES

[75] Inventors: Sumio Nishida, Takarazuka; Yuzuru Sanemitsu, Ashiya, both of Japan

[73] Assignee: Sumitomo Chemical Company, Limited, Osaka, Japan

[21] Appl. No.: 282,562

[22] Filed: Jul. 29, 1994

[30] Foreign Application Priority Data

Jul. 29, 1993  [JP]  Japan .................................. 5-187966

[51] Int. Cl.⁶ .................................................. C07D 277/18
[52] U.S. Cl. .................................................. 548/195
[58] Field of Search ............................................... 548/195

[56] References Cited

U.S. PATENT DOCUMENTS 5,244,863  9/1993  Kawamura et al. .

FOREIGN PATENT DOCUMENTS 0529482  3/1993  European Pat. Off. .
0531970  3/1993  European Pat. Off. .

OTHER PUBLICATIONS

Bailey, Tet letters 30(52) 7457 (1989).
Kuroboshi, Bull Chem Soc Japan 63 1191 (1990).
Ishihara, Chem. Letters, 1990, 211.
Journal of Organic Chem. 14, 747 (1949) "Addition Reactions of Tetrafluoroethylene" by D. D. Coffman et al.

Primary Examiner—Robert Gerstl
Attorney, Agent, or Firm—Birch, Stewart, Kolasch & Birch

[57] ABSTRACT

There is disclosed a process for the production of a fluoroalkanecarboxamide derivative of the formula (I):

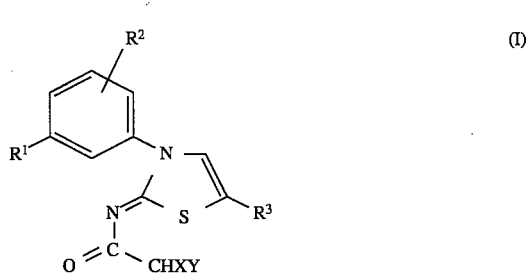

wherein $R^1$ is a halogen atom, an alkyl group substituted with at least one halogen atom or an alkoxyl group substituted with at least one halogen atom; $R^2$ is a hydrogen atom or a halogen atom; and $R^3$ is a methyl group, an ethyl group, a chlorine atom or a bromine atom; X and Y are the same or different and each of them represents a hydrogen atom, a chlorine atom, a fluorine atom or a trifluoromethyl group, with the proviso that X and Y do not simultaneously represent a hydrogen atom or a chlorine atom, which comprises the steps of:

(a) reacting an iminothiazoline compound of the formula (II):

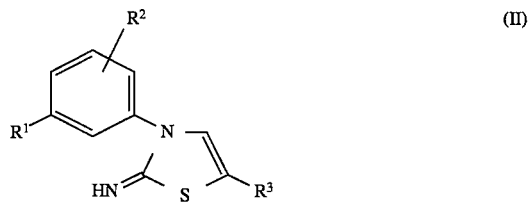

wherein $R^1$, $R^2$ and $R^3$ are each as defined above, or a salt thereof with a fluoroolefin of the formula (III):

$$XYC=CF_2 \qquad (III)$$

wherein X and Y are each as defined above, in the presence of a primary or secondary amine; and
(b) reacting the resultant reaction mixture with water.

10 Claims, No Drawings

PROCESS FOR PRODUCTION OF FLUOROALKANE CARBOXAMIDE DERIVATIVES

FIELD OF THE INVENTION

The present invention relates to a process for the production of fluoroalkanecarboxamide derivatives.

BACKGROUND OF THE INVENTION

A herbicidal difluoroacetamide derivative and its production process are disclosed in the U.S. Pat. No. 5,312,798. However, this process has a drawback in that it requires difluoroacetic acid which can be obtained from tetrafluoroethylene in a few steps-process but cannot readily be produced on an industrial scale (see, e.g., *Org. Prep. Proced. Int.*, 19, 468 (1987)). Accordingly, there has been a great demand for developing an advantageous process for the production of fluoroalkanecarboxamide derivatives.

SUMMARY OF THE INVENTION

The present inventors conducted a research to overcome the drawback of the conventional process and found an advantageous process for the production of fluoroalkanecarboxamide derivatives including the above difluoroacetamide derivative which can provide the desired compound conveniently in one-pot conversion using a readily available fluoroolefin.

Thus, the present invention provides a process for the production of a fluoroalkanecarboxamide derivative of the formula (I):

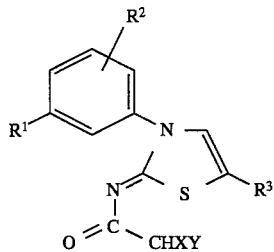

wherein $R^1$ is a halogen atom, an alkyl group substituted with at least one halogen atom or an alkoxyl group substituted with at least one halogen atom; $R^2$ is a hydrogen atom or a halogen atom; and $R^3$ is a methyl group, an ethyl group, a chlorine atom or a bromine atom; X and Y are the same or different and each of them represents a hydrogen atom, a fluorine atom, a chlorine atom or a trifluoromethyl group, with the proviso that X and Y do not simultaneously represent a hydrogen atom or a chlorine atom, which comprises the steps of:

(a) reacting an iminothiazoline compound of the formula (II):

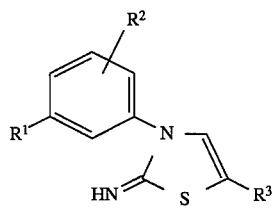

wherein $R^1$, $R^2$ and $R^3$ are each as defined above, or a salt thereof with a fluoroolefin of the formula (III):

$$XYC=CF_2 \quad (III)$$

wherein X and Y are each as defined above, in the presence of a primary or secondary amine compound; and (b) reacting the resultant reaction mixture with water.

DETAILED DESCRIPTION OF THE INVENTION

According to the process of the present invention, fluoroalkanecarboxamide derivatives of the formula (I) can be produced in one-pot conversion using a readily available fluoroolefin.

In the fluoroalkanecarboxamide derivative of the formula (I), as the halogen atom of $R^1$ and $R^2$, there can be exemplified a fluorine atom, a chlorine atom and a bromine atom. The halogen-substituted alkyl groups of $R^1$ include $C_1$–$C_6$ alkyl groups substituted with at least one halogen atom, such as a trifluoromethyl group; and the halogen-substituted alkoxyl groups include $C_1$–$C_6$ alkoxyl groups substituted with at least one halogen atom, such as a difluoromethoxy group, a trifluoromethoxy group, a 1,1,2,2-tetrafluoroethoxy group and a 2,2,2-trifluoroethoxy group. The fluoroalkanoyl group of the formula: $XYCHC=O$ includes a difluoroacetyl group, a chlorofluoroacetyl group, a 2,3,3,3-tetrafluoropropanoyl group and a 2,2-bis(trifluoromethyl)acetyl group.

The fluoroalkanecarboxamide derivative of the formula (I), which can be obtained by the process of the present invention, includes 2-difluoroacetylimino-3-(3-trifluoromethylphenyl)-5-methylthiazoline, 2-difluoroacetylimino-3-(3,5-dichlorophenyl)-5-methylthiazoline, 2-difluoroacetylimino-3-(3-difluoromethoxyphenyl)-5-methylthiazo-line, 2-difluoroacetylimino-3-(3-chlorophenyl)-5-methylthiazoline, 2-difluoroacetylimino-3-(3-trifluoromethoxyphenyl)-5-methylthiazoline, 2-difluoroacetylimino-3-(4-fluoro-3-trifluoromethylphenyl)-5-methylthiazoline, 2-difluoroacetylimino-3-(3-trifluoromethylphenyl)-5-ethylthiazoline, 2-difluoroacetylimino-3-(3-trifluoromethylphenyl)-5-chlorothiazoline, 2-difluoroacetylimino-3-(3-trifluoromethylphenyl)-5-bromothiazoline, 2-chlorofluoroacetylimino-3-(3-trifluoromethylphenyl)-5-methylthiazoline, 2-chlorofluoroacetylimino-3-(3,5-dichlorophenyl)-5-methylthiazoline, 2-chlorofluoroacetylimino-3-(3-difluoromethoxyphenyl)-5-methylthiazoline, 2-chlorofluoroacetylimino-3-(3-chlorophenyl)-5-methylthiazoline, 2-chlorofluoroacetylimino-3-(3-trifluoromethoxyphenyl)-5-methylthiazoline, 2-chlorofluoroacetylimino-3-(4-fluoro-3-trifluoromethylphenyl)-5-methylthiazoline, 2-chlorofluoroacetylimino-3-(3-trifluoromethylphenyl)-5-ethylthiazoline, 2-chlorofluoroacetylimino-3-(3-trifluoromethylphenyl)-5-chlorothiazoline, 2-chlorofluoroacetylimino-3-(3-trifluoromethylphenyl)-5-bromothiazoline, 2-(2,3,3,3-tetrafluoropropanoylimino)- 3-(3-trifluoromethylphenyl)-5-methylthiazoline, 2-(2,3,3,3-tetrafluoropropanoylimino)-3-(3,5-dichlorophenyl)-5-methylthiazoline, 2-(2,3,3,3-tetrafluoropropanoylimino)- 3-(3-difluoromethoxyphenyl)-5-methylthiazoline, 2-(2,3,3,3-tetrafluoropropanoylimino )- 3-(3-chlorophenyl)-5-methylthiazoline, 2-(2,3,3,3-tetrafluoropropanoylimino)-3-(3-trifluoromethoxyphenyl)-5-methylthiazoline, 2-(2,3,3,3-tetrafluoropropanoylimino)- 3-(4-fluoro-3-trifluoromethylphenyl)-5-methylthiazoline, 2-(2,3,3,3-tetrafluoro propanoylimino)- 3-(3-trifluoromethylphenyl)-5-ethylthiazoline, 2-(2,3,3,3-tetrafluoropropanoylimino)- 3-(3-trifluoromethylphenyl)-5-chlorothiazoline, 2-(2,3,3,3-tetrafluoropropanoylimino)-3-(3-trifluoromethylphenyl)-5-bromothiazoline, 2-(2,2-bis(trifluoromethyl)acetylimino)- 3-(3-trifluoromethylphenyl)-5-methylthiazoline, 2-(2,2-bis(trifluoromethyl)acetylimino)- 3-(3,5-dichlorophenyl)-5-methylthiazoline, 2-(2,2-bis(trifluoromethyl)acetylimino)- 3-(3-difluoromethoxyphenyl)-5-methylthiazoline, 2-(2,2-bis(trifluoromethyl)acetylimino)- 3-(3-chlorophenyl)-5-methylthiazoline, 2-(2,2-bis(trifluoromethyl)acetylimino)- 3-(3-trifluoromethoxyphenyl)-5-methylthiazoline, 2-(2,2-bis(trifluoromethyl)acetylimino)- 3-(4-fluoro-3-trifluoromethylphenyl)-5-methylthiazoline, 2-(2,2-bis(trifluoromethyl)acetylimino)- 3-(3-trifluoromethylphenyl)-5-ethylthiazoline, 2-(2,2-bis(trifluoromethyl)acetylimino)- 3-(3-trifluoromethylphenyl)-5-chlorothiazoline and 2-(2,2-bis (trifluoromethyl)acetylimino)- 3-(3-trifluoromethylphenyl)-5-bromothiazoline.

The step (a) of the present process is conducted in the presence of a primary or secondary amine compound. The primary amine compound and the secondary amine compound to be used in the present invention may be substituted with an inert group and are not limited to specific compounds as long as they can be added to the fluoroolefin.

The primary amine compound and the secondary amine compound include a primary monoamine and a secondary monoamine, respectively.

The primary monoamine compound is represented by the formula (IV):

$$Q-NH_2 \qquad (IV)$$

wherein Q is an alkyl of 1 to 20 carbon atoms, an alkoxyalkyl of 3 to 10 carbon atoms, an alkylthioalkyl of 3 to 10 carbon atoms, a cycloalkyl of 3 to 10 carbon atoms, a cycloalkylalkyl of 3 to 10 carbon atoms, an alkenyl of 3 to 10 carbon atoms, an alkynyl of 3 to 10 carbon atoms, an aralkyl of 7 to 10 carbon atoms, a heteroaralkyl of 6 to 10 carbon atoms, a heteroaryl of 5 to 10 carbon atoms or an aryl of 6 to 12 carbon atoms.

Preferred examples of the primary monoamine compound are methylamine, ethylamine, n-propylamine, isopropylamine, n-butylamine, isobutylamine, sec-butylamine, tert-butylamine, n-pentylamine, n-hexylamine, n-octylamine, 2-ethylhexylamine, dodecylamine, tetradecylamine, octadecylamine, eicosylamine, 2-methoxyethylamine, 2-ethoxyethylamine, 3-methoxypropylamine, 3-ethoxypropylamine, 2-methylthioethylamine, cyclopropylamine, cyclopentylamine or cyclohexylamine, cyclohexylmethylamine, allylamine, propargylamine, benzylamine, phenethylamine, 3-phenyl-1-propylamine, 4-phenyl-1-butylamine, 2-aminomethylpyridine, aminopyridines, aniline and naphthylamine.

The secondary monoamine compound may be represented by the formula (V):

$$Q-NH-Q \qquad (V)$$

wherein Q's are the same or different and are each as defined above, and both Q groups may form together a —(CH$_2$)$_4$— group, a —(CH$_2$)$_5$— group or a —(CH$_2$)$_2$—O—(CH$_2$)$_2$— group where each alkylene group may be substituted with at least one C$_1$–C$_3$ alkyl group.

Preferred examples of the secondary monoamine compound are dimethylamine, diethylamine, di-n-propylamine, diisopropylamine, di-n-butylamine, diisobutylamine, dipentylamine, dihexylamine, diallyamine, dicyclohexylamine, N-ethylmethylamine, N-methylpropylamine, N-methylisopropylamine, N-methylbutylamine, N-methylhexylamine, N-methylcyclohexylamine, N-ethylpropylamine, N-ethylisopropylamine, N-ethylbutylamine, N-ethylhexylamine, N-ethylcyclohexylamine, N-methylbenzylamine, N-ethylbenzylamine, dibenzylamine, N-methylaniline, N-ethylaniline and N-propylaniline; and cyclic amines such as pyrrolidine, piperidine, pipecoline and morpholine.

In addition, the primary amine compound and the secondary amine compound include a primary polyamine compound and a secondary polyamine compound, respectively.

The primary polyamine compound and the secondary polyamine compound may be represented by the formula (VI):

$$Q_2N-Z-N-L_2 \qquad (VI)$$

wherein Z is a phenylene group, a —(CH$_2$)$_2$— group or a —(CH$_2$)$_3$— group; Q's are the same or different and are each as defined above; L's are the same as Q; and both Q groups and both L groups may form a —(CH$_2$)$_2$—NH—(CH$_2$)2— group where each alkylene group may be substituted with at least one C$_1$–C$_3$ alkyl group; and at least one of the Q and L groups is a hydrogen atom.

Preferred examples of the primary polyamine compound or the secondary polyamine compound are ethylenediamine derivatives such as ethylenediamine, N-methylethylenediamine, N,N-dimethylethylenediamine, N,N'-dimethylethylenediamine, N,N,N'-trimethylethylenediamine, N-ethylethylenediamine, N,N-diethylethylenediamine, N,N'-diethylethylenediamine, N,N,N'-triethylethylenediamine, N,N-dimethyl-N'-ethylethylenediamine, N,N-diethyl-N'-methylethylenediamine, N-propylethylenediamine; propanediamine derivatives such as N-methyl-1,3-propanediamine, N,N-dimethyl-1,3-propanediamine, N,N'-dimethyl-1,3-propanediamine, N,N-diethyl-1,3-propanediamine, N,N'-diethyl-1,3-propanediamine, N,N-dibutyl-1,3-propanediamine and N,N,N'-trimethyl-1,3-propanediamine; piperazine, N-methylpiperazine, 2-methylpiperazine, 1-(2-aminoethyl)piperidine, 4-(2-aminoethyl)morpholine, 1-(2-aminoethyl)-pyrolidine, 1-(2-aminoethyl)piperazine, 2-(2-aminoethyl)pyridine, 4-(3-aminopropyl)-morpholine or 1-(3-aminopropyl)pipecoline; and aromatic polyamines such as phenylenediamine.

Moreover, acetaldehyde ammonia and 1,3-di-(4-piperidyl)propane which are not included in the above formula (VI) can be exemplified as the secondary polyamine compound.

The fluoroolefin of the formula (III) includes trifluoroethylene, tetrafluoroethylene, hexafluoropropene, octafluoroisobutene and chlorotrifluoroethylene. These fluoroolefines are commercially available.

A base may be used, if necessary, in the present invention, and is not limited to a specific one as long as it can catch hydrogen fluoride formed by the reaction. The primary amine or the secondary amine may be used as the base as it is. Other usable bases include inorganic bases such as alkali metal hydroxides and alkaline earth metal hydroxides (e.g., sodium hydroxide, potassium hydroxide), alkali metal carbonates and alkaline earth metal carbonates (e.g., sodium carbonate, potassium carbonate), and alkali metal hydrogencarbonates; and organic bases such as triethylamine, N,N-dimethylaniline, N,N-diethylaniline, pyridine and quinoline.

The step (a) can be conducted in the presence of a solvent, if necessary. The solvent to be used is an aprotic polar solvent such as N,N-dimethylformamide, N,N-dimethylacetamide, N-methylpyrrolidone or dimethylsulfoxide; an alkylnitrile solvent such as acetonitrile or propionitrile; an ether solvent such as tetrahydrofuran, dimethoxyethane, diglyme or triglyme; a halogenated solvent such as chloroform or dichloroethane; or an aromatic hydrocarbon solvent such as benzene, toluene or monochlorobenzene; or a mixed solvent thereof. However, the solvent is not limited to those described above.

The reaction temperature of the step (a) is usually in the range of 0° C. to 200° C., preferably 20° C. to 150° C. or the boiling point of the solvent. As for the amount of the reactants, 1 to 10 moles of the primary amine compound or the secondary amine compound is usually used to 1 mole of the iminothiazoline compound of the formula (II) shown above; the amount of the base to be used, if necessary, is usually 1 to 10 moles; and 1 to excess moles of fluoroolefin is usually used in the step (a). The reaction can be effected at atmospheric pressure or at a pressure of 1 kg/cm$^2$ to 10 kg/cm$^2$ (gauge).

In the present invention, the step (a) is usually conducted by adding the fluoroolefin of the formula (III) to a solution of the iminothiazoline compound of the formula (II) and the primary amine compound or the secondary amine compound, or the step (a) can be conducted by the following steps:

(i) reacting the fluoroolefin with a primary amine compound or a secondary amine compound; and (ii) reacting the resultant reaction mixture with the iminothiazoline compound of the formula (II).

The resultant reaction mixture in the step (ii) above is then reacted with water to obtain the desired compounds. Because the step (b) is usually conducted successively after the step (a), the step (b) may be conducted in the presence of the same solvent used in step (a); however, a solvent to be used in the step (b) may be optionally selected from the solvents that can be used in the step (a).

In the step (b), the reaction temperature is usually in the range of 0° C. to 100° C. or the boiling point of the solvent. The amount of water is usually 1 to excess moles to 1 mole of the iminothiazoline compound of the formula (II).

After completion of the step (b), the reaction mixture is subjected to usual post-treatments such as extraction with an organic solvent and/or concentration to obtain the compounds of the present invention. The obtained compound can be further purified, if necessary, by an operation such as recrystallization or column chromatography.

The iminothiazoline compound of the formula (II), which is the raw material of the present invention, can be obtained by the process as described in the specification of the Japanese Patent Application No. 325,259/1992 or the U.S. Pat. No. 5,312,798.

In the iminothiazoline compound of the formula (II), as the halogen atom, there can be exemplified a fluorine atom, a chlorine atom and a bromine atom. The halogen-substituted alkyl groups include $C_1$–$C_6$ alkyl groups substituted with at least one halogen atom, such as a trifluoromethyl group; and the halogen-substituted alkoxyl groups include $C_1$–$C_6$ alkoxyl groups substituted with at least one halogen atom, such as a difluoromethoxy group, a trifluoromethoxy group, a 1,1,2,2-tetrafluoroethoxy group and a 2,2,2-trifluoroethoxy group.

The iminothiazoline compound of the formula (II) includes 2-imino-3-(3-trifluoromethylphenyl)- 5-methylthiazoline, 2-imino-3-(3,5-dichlorophenyl)-5-methylthiazoline, 2-imino-3-(3-difluoromethoxyphenyl)-5-methylthiazoline, 2-imino-3-(3-chlorophenyl)- 5-methylthiazoline, 2-imino-3-(3-trifluoromethoxyphenyl)-5-methylthiazoline, 2-imino-3-(4-fluoro-3-trifluoromethylphenyl)-5-methylthiazoline, 2-imino-3-(3-trifluoromethylpehnyl)-5-ethylthiazoline, 2-imino-3-(3-trifluoromethylphenyl)-5-chlorothiazoline and 2-imino-3-(3-trifluoromethylphenyl)-5-bromothiazoline. In addition, a salt of an inorganic acid such as hydrochloric acid or an organic acid and the above-described compound can be used in the present reaction.

Next, the present invention will be further illustrated by the following examples; however, they are not to be construed to limit the scope of the present invention.

EXAMPLE 1

A solution of 2-imino-3-(3-trifluoromethylphenyl)-5-methylthiazoline (0.77 g, 3.0 mmol), diethylamine (1.06 g, 14.5 mmol) and triethylamine (0.91 g, 9.0 mmol) in N,N-dimethylformamide (15 ml) charged in a reaction flask was reacted with tetrafluoroethylene, which was made to flow into the flask (ca. 0.3 liter/hr), with vigorous stirring at 50° C. for 17 hours. After cooling to an ambient temperature, the reaction mixture was poured into ice-water, and extracted with ethyl acetate. The ethyl acetate layer was washed with water and then brine, and dried over anhydrous magnesium sulfate. The solvent was distilled off, and the residue was subjected to silica gel column chromatography (eluent, n-hexane: ethyl acetate=2:1), which afforded 2-difluoroacetylimino-3-(3 -trifluoromethylphenyl)-5-methylthiazoline (0.82 g, 2.4 mmol, yield 81%).

m.p., 123.9° C.;

$^1$H NMR (CDCl$_3$, TMS) δ (ppm): 2.39 (s, 3H), 5.89 (t, 1H, J=54.9 Hz), 6.97 (s, 1H), 7.6–7.8 (m, 4H).

EXAMPLE 2

A solution of 2-imino-3-(3-trifluoromethylphenyl)-5-methylthiazoline (0.52 g, 2.0 mmol), piperidine (0.51 g, 6.0 mmol) and triethylamine (0.61 g, 6.0 mmol) in N,N-dimethylformamide (10 ml) charged in a reaction flask was reacted with tetrafluoroethylene, which was made to flow intothe flask (ca. 0.3 liter/hr), with vigorous stirring at 50° C. for 9 hours. After cooling to an ambient temperature, the reaction mixture was poured into ice-water, and extracted with ethyl acetate. The ethyl acetate layer was washed with water and then brine, and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (0.61 g, 1.8 mmol, yield 91%).

EXAMPLE 3

A solution of 2-imino-3-(3-trifluoromethylphenyl)-5-methylthiazoline (0.52 g, 2.0 mmol), piperidine (0.51 g, 6.0 mmol) and triethylamine (0.61 g, 6.0 mmol) in toluene (10 ml) charged in a reaction flask was reacted with tetrafluoroethylene, which was made to flow intothe flask (ca. 0.3 liter/hr), with vigorous stirring at 50° C. for 15 hours. After cooling to an ambient temperature, the reaction mixture was poured into ice-water, and extracted with toluene. The toluene layer was washed with water and then brine, and dried over anhydrous magnesium sulfate. The solvent was distilled off, and the residue was subjected to silica gel column chromatography, which afforded 2-difluoroacetylimino- 3(3-trifluoromethylphenyl)-5-methylthiazoline (0.48 g, 1.4 mmol, yield 71%).

EXAMPLE 4

A solution of 2-imino-3-(3-trifluoromethylphenyl)-5-methylthiazoline (0.52 g, 2.0 mmol), n-butylamine (0.44 g, 6.0 mmol) and triethylamine (0.6 1 g, 6.0 mmol) in N,N-dimethylformamide (10 ml) charged in a reaction flask was reacted with tetrafluoroethylene, which was made to flow intothe flask (ca. 0.3 liter/hr), with vigorous stirring at 50° C. for 13 hours. After cooled to an ambient temperature, the reaction mixture was poured into ice-water, and extracted with diethyl ether. The ether layer was washed with 5% hydrochloric acid, water and then brine, and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (0.50 g, 1.5 mmol, yield 74%).

EXAMPLE 5

A solution of 2-imino-3-(3-trifluoromethylphenyl)-5-methylthiazoline (0.52 g, 2.0 mmol), diethylamine (0.44 g, 6.0 mmol), triethylamine (0.61 g, 6.0 mmol) in N,N-dimethylformamide (10 ml) charged in a reaction flask was reacted with tetrafluoroethylene in the flask atmosphere (0.70 g, 7.0 mmol), which was supplied from a balloon tothe flask, at 50° C. for 21 hours. After cooling to an ambient temperature, the reaction mixture was poured into ice-water, and extracted with ethyl acetate. The ethyl acetate layer was washed with water and then brine, and dried over anhydrous magnesium sulfate. The solvent was distilled off, and the residue was subjected to silica gel column chromatography, which afforded 2-difluoroacetylimino-3(3-trifluoromethylphenyl)-5-methylthiazoline (0.44 g, 1.3 mmol, yield 65%).

EXAMPLE 6

A solution of 2-imino-3-(3-trifluoromethylphenyl)-5-methylthiazoline hydrochloride (1.47 g, 5.0 mmol), piperidine (0.64 g, 7.5 mmol) and triethylamine (1.77 g, 17.5 mmol) in N,N-dimethylformamide (10 ml) charged in a reaction flask was reacted with tetrafluoroethylene, which was made to flow intothe flask (ca. 0.7 liter/hr), with vigorous stirring at 50° C. for 13 hours. After cooling to an ambient temperature, the reaction mixture was poured into ice-water, and extracted with diethyl ether. The ether layer was washed with water and then brine, and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (1.56 g, 4.6 mmol, yield 93%).

EXAMPLE 7

A solution of 2-imino-3-(3-trifluoromethylphenyl)-5-methylthiazoline (0.77 g, 3.0 mmol), diethylamine (1.32 g, 18.0 mmol) and potassium carbonate (1.04 g, 7.5 mmol) in N,N-dimethylformamide (15 ml) charged in a reaction flask was reacted with tetrafluoroethylene, which was made to flow intothe flask (ca. 0.3 liter/hr), with vigorous stirring at 50° C. for 32 hours. After cooling to an ambient temperature, the reaction mixture was poured into ice-water, and extracted with ethyl acetate. The ethyl acetate layer was washed with water and then brine, and dried over anhydrous magnesium sulfate. The solvent was distilled off, and the residue was subjected to silica gel column chromatography, which afforded 2-difluoroacetylimino-3-(3-trifluoromethylphenyl)- 5-methylthiazoline (0.53 g, 1.6 mmol, yield 53%).

EXAMPLE 8

A solution of 2-imino-3-(3-trifluoromethylphenyl)-5-methylthiazoline (1.29 g, 5.0 mmol) and piperidine (0.64 g, 7.5 mmol) in N,N-dimethylformamide (10 ml) was reacted in a reaction flask with tetrafluoroethylene, which was made to flow into the flask (ca. 0.7 liter/hr), with vigorous stirring at 50° C. for 21 hours. After cooling to an ambient temperature, the reaction mixture was poured into ice-water, and extracted with diethyl ether. The diethyl ether layer was washed with water and then brine, and dried over magnesium sulfate. The solvent was distilled off, and the residue was subjected to silica gel column chromatography, which afforded 2-difluoroacetylimino-3-(3-trifluoromethylphenyl)- 5-methylthiazoline (1.24 g, 3.7 mmol, yield 74%). Unreacted part of 2-imino-3-(3-trifluoromethylphenyl)-5-methylthiazoline (0.30 g) was recovered.

EXAMPLE 9

A solution of 2-imino-3-(3-trifluoromethylphenyl)-5-methylthiazoline (1.29 g, 5.0 mmol) and 3-(N,N-dimethylamino)propylamine (0.77 g, 7.5 mmol) in N,N-dimethylformamide (10 ml) charged in a reaction flask was reacted with tetrafluoroethylene, which was made to flow intothe flask (ca. 0.3 liter/hr), with vigorous stirring at 50° C. for 17 hours. After cooling to an ambient temperature, the reaction mixture was poured into ice-water, and extracted with diethyl ether. The diethyl ether layer was washed with water and then brine, and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (0.59 g, 1.8 mmol, yield 35%). Unreacted part of 2-imino-3-(3-trifluoromethylphenyl)-5-methylthiazoline (0.50 g) was recovered.

EXAMPLE 10

A solution of 2-imino-3-(3-trifluoromethylphenyl)-5-methylthiazoline (1.29 g, 5.0 mmol) and piperazine (0.65 g, 7.5 mmol) in N,N-dimethylformamide (10 ml) charged in a reaction flask was reacted with tetrafluoroethylene, which was made to flow into the flask (ca. 0.7 liter/hr), with vigorous stirring at 50° C. for 9 hours. After cooling to an ambient temperature, the reaction mixture was poured into ice-water, and extracted with diethyl ether. The ether layer was washed with water and then brine, and dried over anhydrous magnesium sulfate. The solvent was distilled off, and the residue was subjected to silica gel column chromatography, which afforded 2-difluoroacetylimino- 3-(3-trifluoromethylphenyl)-5-methylthiazoline (1.24 g, 3.7 mmol, yield 74%).

EXAMPLE 11

A solution of 2-imino-3-(3-trifluoromethylphenyl)-5-methylthiazoline hydrochloride salt (1.47 g, 5.0 mmol), piperazine (0.64 g, 7.5 mmol) and triethylamine (1.52 g, 15.0 mmol) in diglyme (10 ml) charged in a reaction flask was reacted with tetrafluoroethylene, which was made to flow intothe flask (ca. 0.7 liter/hr), with vigorous stirring at 70° C. for 24 hours. After cooling to an ambient temperature, the reaction mixture was poured into ice-water, and extracted with diethyl ether. The diethyl ether layer was washed with water and then brine, and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (1.01 g, 3.0 mmol, yield 60%).

EXAMPLE 12

A solution of 2-imino-3-(3-trifluoromethylphenyl)-5-methylthiazoline (1.29 g, 5.0 mmol) and 1-(2-aminoethyl)piperazine (0.78 g, 6.0 mmol) in N,N-dimethylformamide (10 ml) charged in a reaction flask was reacted with tetrafluoroethylene, which was made to flow into the flask (ca. 0.7 liter/hr), with vigorous stirring at 50° C. for 33 hours. After cooling to an ambient temperature, the reaction mixture was poured into saturated aqueous sodium carbonate solution, and extracted with diethyl ether. The diethyl ether layer was washed with water and then brine, and dried over anhydrous magnesium sulfate. The solvent was distilled off, and the residue was subjected to silica gel column chromatography, which afforded 2-difluoroacetylimino-3-(3-trifluoromethylphenyl)- 5-methylthiazoline (1.18 g, 3.5 mmol, yield 70%). Unreacted part of 2-imino-3-(3-trifluoromethylphenyl)-5-methylthiazoline (0.12 g) was recovered.

EXAMPLE 13

A solution of 2-imino-3-(3-trifluoromethylphenyl)-5-methylthiazoline (1.29 g, 5.0 mmol) and piperazine (0.52 g, 6.0 mmol) in toluene (10 ml) charged in a reaction flask was reacted with tetrafluoroethylene, which was made to flow intothe flask (ca. 0.7 liter/hr), with vigorous stirring at 80° C. for 48 hours. After cooling to an ambient temperature, the reaction mixture was poured into saturated aqueous sodium carbonate solution, and extracted with toluene. The toluene layer was washed with water and then brine, and dried over anhydrous magnesium sulfate. The solvent was distilled off, and the residue was subjected to silica gel column chromatography, which afforded 2-difluoroacetylimino- 3-(3-trifluoromethylphenyl)-5-methylthiazoline (1.29 g, 3.8 mmol, yield 77% ).

EXAMPLE 14

A solution of 2-imino-3-(3-trifluoromethylphenyl)-5-methylthiazoline hydrochloride (1.47 g, 5.0 mmol) and morpholine (1.57 g, 18.0 mmol) in N,N-dimethylformamide (10 ml) charged in a reaction flask was reacted with tetrafluoroethylene, which was made to flow intothe flask (ca. 0.7 liter/hr), with vigorous stirring at 60° C. for 2 hours. After cooling to an ambient temperature, the reaction mixture was poured into saturated aqueous sodium hydrogencarbonate solution (100 ml), and extracted twice with toluene (100 ml×2). The toluene layer was washed twice with 5% hydrochloric acid (50 ml×2) and water (70 ml) and then brine (70 ml), and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (1.47 g, 4.4 mmol, yield 87%).

EXAMPLE 15

A solution of 2-imino-3-(3-trifluoromethylphenyl)-5-methylthiazoline (1.29 g, 5.0 mmol) and morpholine (0.96 g, 11.0 mmol) in N,N-dimethylformamide (10 ml) charged in a reaction flask was reacted with tetrafluoroethylene, which was made to flow into the flask (ca. 0.7 liter/hr), with vigorous stirring at 50° C. for 13 hours. After cooling to an ambient temperature, the reaction mixture was poured into a saturated aqueous sodium hydrogencarbonate solution (100 ml), and extracted twice with toluene (100 ml×2). The toluene layer was washed twice with 5% hydrochloric acid (50 ml×2) and water (50 ml) and then brine (50 ml), and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (1.64 g, 4.9 mmol, yield 98%).

EXAMPLE 16

A solution of piperidine (0.57 g, 6.7 mmol) in N,N-dimethylformamide (10 ml) charged in a reaction flask was reacted with tetrafluoroethylene, which was made to flow into the flask (ca. 0.7 liter/hr), with vigorous stirring at 50° C. for 10 hours. After cooling to an ambient temperature, 2-imino-3-(3-trifluoromethylphenyl)-5-methylthiazoline hydrochloride (1.29 g, 5.0 mmol) was added tothe reaction mixture and allowed to react overnight at room temperature and then at 50° C. for 8 hours. After cooling to an ambient temperature, the reaction solution was poured intoa saturated aqueous sodium hydrogencarbonate solution, and extracted twice with toluene (100 ml×2). The toluene layer was washed twice with 5% hydrochloric acid (50 ml×2) and water (50 ml) and then brine (50 ml), and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (0.83 g, 2.5 mmol, yield 49%).

The aqueous hydrochloric acid layer separated after washing was neutralized and then made alkaline with 32% sodium hydroxide under ice-water cooling, after which the solution was extracted twice with diethyl ether (100 ml×2). The ether layer was dried over anhydrous magnesium sulfate, and the solvent was removed under reduced pressure. In this way, 2-imino-3-(3-trifluoromethylphenyl)-5-methylthiazoline (0.62 g) was recovered.

EXAMPLE 17

A solution of 2-imino-3-(3-trifluoromethylphenyl)-5-methylthiazoline (0.64 g, 2.5 mmol) and morpholine (0.48 g, 5.5 mmol) in acetonitrile (5 ml) charged in a reaction flask was reacted with tetrafluoroethylene, which was made to flow intothe flask (ca. 0.7 liter/hr), with vigorous stirring at 50° C. for 13 hours. After cooling to an ambient temperature, the reaction solution was poured intoa saturated aqueous sodium hydrogen-carbonate solution (50 ml), and extracted twice with toluene (50 ml×2). The toluene layer was washed twice with 5% hydrochloric acid (30 ml×2) and water (50 ml) and then brine (50 ml), and dried over anhydrous magnesium sulfate. The solvent was distilled off, and the residue was subjected to silica gel column chromatography, which afforded 2-difluoroacetylimino-3-(3-trifluoromethylphenyl)-5-methylthiazoline (0.64 g, 1.9 mmol, yield 76%).

EXAMPLE 18

A solution of piperidine (1.70 g, 20.0 mmol) in acetonitrile (10 ml) charged in a reaction flask was reacted with tetrafluoroethylene, which was made to flow into the flask (ca. 0.7 liter/hr), with vigorous stirring at room temperature for 7.5 hours. After cooling to an ambient temperature, 2-imino-3-(3-trifluoromethylphenyl)-5-methylthiazoline hydrochloride (5.89 g, 20.0 mmol) and acetonitrile (25 ml) were added to the reaction mixture and allowed to react at room temperature overnight. After cooling to an ambient temperature, the reaction solution was poured intoa saturated aqueous sodium hydrogen-carbonate solution, and extracted three times with toluene (100 ml×3). The combined toluene layer was washed twice with 10% hydrochloric acid (100 ml×2) and water (100 ml) and then brine (100 ml), and dried over anhydrous magnesium sulfate. The solvent was distilled off, and the residue was subjected to silica gel column chromatography, which afforded 2-difluoroacetylinfino-3-(3-trifluoromethylphenyl)-5-methylthiazoline (5.33 g, 15.9 mmol, yield 79%).

The aqueous hydrochloric acid layer separated after washing was neutralized and then made alkaline with 32% sodium hydroxide under ice-water cooling, after which the solution was extracted twice with diethyl ether (100 ml×2). The ether layer was dried over anhydrous magnesium sulfate, and the solvent was removed under reduced pressure. In this way, 2-imino-3-(3-trifluoromethylphenyl)-5-methylthiazoline (0.75 g) was recovered.

EXAMPLE 19

A solution of 2-imino-3-(3-trifluoromethylphenyl)-5-methylthiazoline (2.28 g, 8.8 mmol) and piperidine (0.98 g, 11.5 mmol) in N,N-dimethylformamide (10 ml) charged in a reaction flask was reacted with tetrafluoroethylene, which was made to flow into the flask (ca. 0.7 liter/hr), with vigorous stirring at room temperature for 60 hours. After cooling to an ambient temperature, the reaction mixture was poured intoa saturated aqueous sodium hydrogencarbonate solution (100 ml), and extracted twice with toluene (100 ml×2). The combined toluene layer was washed twice with 5% hydrochloric acid (50 ml×2) and water (70 ml) and then brine (70 ml), and dried over anhydrous magnesium sulfate. The solvent was distilled off, and the residue was subjected to silica gel column chromatography, which afforded 2-difluoroacetylimino-3-(3-trifluoromethylphenyl)- 5-methylthiazoline (2.32 g, 6.9 mmol, yield 78%).

The aqueous hydrochloric acid layer separated after washing was neutralized and then made alkaline with 32% sodium hydroxide under ice-water cooling, after which the solution was extracted twice with diethyl ether (100 ml×2). The ether layer was dried over anhydrous magnesium sulfate, and the solvent was removed under reduced pressure. In this way, 2-imino-3-(3-trifluoromethylphenyl)-5-methylthiazoline (0.34 g) was recovered.

EXAMPLE 20

A solution of 2-imino-3-(3-trifluoromethylphenyl)-5-methylthiazoline hydrochloride (1.47 g, 5.0 mmol), triethylamine (2 ml) and N-methylaniline (1.29 g, 12.0 mmol) in N,N-dimethylformamide (10 ml) charged in a reaction flask was reacted with tetrafluoroethylene, which was made to flow into the flask (ca. 0.7 liter/hr), with vigorous stirring at 80° C. for 30 hours. After cooling to an ambient temperature, the reaction mixture was poured intoa saturated aqueous sodium hydrogencarbonate solution (100 ml), and extracted twice with toluene (100 ml×2). The combined toluene layer was washed twice with 10% hydrochloric acid (50 ml×2) and water (70 ml) and then brine (70 ml), and dried over anhydrous magnesium sulfate. The solvent was distilled off, and the residue was subjected to silica gel column chromatography, which afforded 2-difluoroacetylimino-3-(3 -trifluoromethylphenyl)-5-methylthiazoline (0.45 g, 1.34 mmol, yield 27%).

The aqueous hydrochloric acid layer separated after washing was neutralized and then made alkaline with 32% sodium hydroxide under ice-water cooling, after which the solution was extracted twice with diethyl ether (100 ml×2). The ether layer was dried over anhydrous magnesium sulfate, and the solvent was removed under reduced pressure. In this way, 2-imino-3-(3-trifluoromethylphenyl)-5-methylthiazoline (0.50 g) was recovered.

EXAMPLE 21

A solution of 2-imino-3-(3-trifluoromethylphenyl)-5-methylthiazoline (1.29 g, 5.0 mmol) and diethylamine (0.51 g, 7.0 mmol) in N,N-dimethylformamide (10 ml) charged in a reaction flask was reacted with hexafluoropropene in the flask atmosphere, which was supplied from a balloon to the flask, with vigorous stirring at room temperature for 3.5 hours. After completion of the reaction, the reaction mixture was subjected to a similar post-treatment as described above, which afforded 2-(2,3,3,3-tetrafluoropropanoylimino)-3-(3-trifluoromethylphenyl)-5-methylthiazoline (1.48 g, 3.8 mmol, yield 77%).

m.p., 162.0° C.; $^1$H NMR (CDCl$_3$, internal standard TMS) δ (ppm): 2.40 (s, 3H), 5.10 (dq, 1H, J=47.1, 7.7 Hz), 6.98 (s, 1H), 7.6–7.9 (m, 4H).

EXAMPLE 22

In this example, 2-fluoroacetylimino-3-(3-trifluoromethylphenyl)-5-methylthiazoline is obtained in the same manner as described in Example 15, except that trifluoroethylene is used in place of tetrafluoroethylene.

EXAMPLE 23

In this example, 2-(2,2-bis(trifluoromethyl)acetylimino)-3-(3-trifluoromethylphenyl)- 5-methylthiazoline was obtained in the same manner as described in Example 15, except that octafluoroisobutene is used in place of tetrafluoroethylene.

EXAMPLE 24

A solution of 2-imino-3-(3-trifluoromethylphenyl)-5-methylthiazoline (1.29 g, 5.0 mmol) and diethylamine (1.21 g, 16.5 mmol) in N,N-dimethylformamide (10 ml) charged in a reaction flask was reacted with the chlorotrifluoloethylene, which was made to flow into the flask (ca. 0.7 liter/hr), with vigorous stirring at room temperature for 6 hours. After completion of the reaction, the reaction mixture was subjected to a similar post-treatment as described above, which afforded 2-chlorofluoroacetylimino)-3-(3-trifluoromethylphenyl)-5-methylthiazoline (1.19 g, 3.4 mmol, yield 67% ).

m.p., 155.4° C.; $^1$H NMR (CDCl$_3$, internal standard TMS) δ (ppm): 2.40 (s, 3H), 6.34 (d, 1H, J=51.4 Hz) 6.98 (s, 1H), 7.6–7.9 (m, 4H).

What is claimed is:

1. A process for the production of a fluoroalkanecarboxamide derivative of the formula (I):

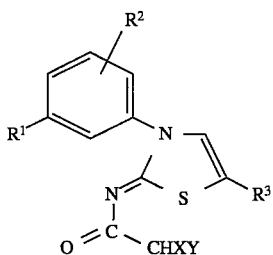

(I)

wherein $R^1$ is a halogen atom, an alkyl group substituted with at least one halogen atom or an alkoxyl group substituted with at least one halogen atom; $R^2$ is a hydrogen atom or a halogen atom; and $R^3$ is a methyl group, an ethyl group, a chlorine atom or a bromine atom; X and Y are the same or different and each of them represents a hydrogen atom, a chlorine atom, a fluorine atom or a trifluoromethyl group, with the proviso that X and Y do not simultaneously represent a hydrogen atom or a chlorine atom, which comprises the steps of:

(a) reacting an iminothiazoline compound of the formula (II):

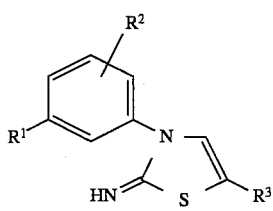

(II)

wherein $R^1$, $R^2$ and $R^3$ are each as defined above, or a salt thereof with a fluoroolefin of the formula (III):

 (III)

wherein X and Y are each as defined above, in the presence of 1 to 10 moles of a primary or secondary amine compound to 1 mole of the iminothiazoline compound of the formula (II); and (b) reacting the resultant reaction mixture with water.

2. A process according to claim 1, wherein the reaction is effected in the presence of a base.

3. A process according to claim 1, wherein the step (a) is conducted by reacting the fluoroolefin III with a primary amine compound or a secondary amine compound, and then reacting the resultant reaction mixture with the iminothiazoline compound II.

4. A process according to claim 1, wherein said primary amine compound is represented by the formula (IV):

 (IV)

wherein Q is selected from the group consisting of alkylamines of 1 to 20 carbon atoms, alkoxyalkylamines of 3 to 10 carbon atoms, alkylthioalkylamines of 3 to 10 carbon atoms, cycloalkylamines of 3 to 10 carbon atoms, cycloalkylalkylamines of 3 to 10 carbon atoms, alkenylamines of 3 to 10 carbon atoms, alkynylamines of 3 to 10 carbon atoms, aralkyamines of 7 to 10 carbon atoms, heteroaralkylamines of 6 to 10 carbon atoms, heteroarylamines of 5 to 10 carbon atoms and arylamines of 6 to 12 carbon atoms; said secondary amine compound is represented by the formula (V):

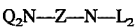 (V)

wherein Q's are the same or different and are each as defined above, and both Q groups may form together a —$(CH_2)_4$— group, a —$(CH_2)_5$— group or a —$(CH_2)_2$—O—$(CH_2)_2$— group where each alkylene group may be substituted with at least one $C_1$–$C_3$ alkyl group; or said primary amine compound or said secondary amine compound is represented by the formula:

$Q_2N$—Z—N—$L_2$ wherein Z is a phenylene group, a —$(CH_2)_2$— group or a —$(CH_2)_3$— group; wherein the Q groups are the same as defined for the Q groups above; wherein the L groups are the same as defined for the Q groups or a hydrogen atom; and both the Q groups together or both the L groups together may form a —$(CH_2)_2$—NH—$(CH_2)_2$— group where each alkylene group may be substituted with at least one $C_1$–$C_3$ alkyl group; provided that at least one of the L groups is a hydrogen atom.

5. A process according to claim 1, wherein the primary amine compound is selected from the group consisting of methylamine, ethylamine, n-propylamine, isopropylamine, n-butylamine, isobutylamine, sec-butylamine, tert-butylamine, n-pentylamine, n-hexylamine, 2-ethylhexylamine, n-octylamine, dodecylamine, tetradecylamine, octadecylamine, eicosylamine, 2-methoxyethylamine, 2-ethoxyethylamine, 3-methoxypropylamine, 3-ethoxypropylamine, 2-methylthioethylamine cyclohexylmethylamine, cyclopentylamine, cyclohexylamine, allylamine, propargylamine, benzylamine, phenethylamine, 3-phenyl-1-propylamine, 4-phenyl-1-butylamine and aniline; and the secondary amine compound is selected from the group consisting of dimethylamine, diethylamine, di-n-propylamine, diisopropylamine, di-n-butylamine, diisobutylamine, dipentylamine, dihexylamine, diallylamine, dicyclohexylamine, N-ethylmethylamine, N-methylpropylamine, N-methylisopropylamine, N-methylbutylamine, N-methylhexylamine, N-methylcyclohexylamine, N-ethylpropylamine, N-ethylisopropylamine, N-ethylbutylamine, N-ethylhexylamine, N-ethylcyclohexylamine, N-methylbenzylamine, N-ethylbenzylamine, dibenzylamine, N-methylaniline, N-proplaniline, pyrrolidine, piperidine, pipecoline, morpholine, cyclopropylamine, 2-aminomethylpyridine, aminopyridines and naphthylamine.

6. A process according to claim 1, wherein the primary amine compound or the secondary amine compound is selected from the group consisting of ethylenediamine, N-methylethylenediamine, N,N-dimethylethylenediamine, N,N'-dimethylethylenediamine, N,N,N'-trimethylethylenediamine, N-ethylethylenediamine, N,N-diethylethylenediamine, N,N'-diethylethylenediamine, N,N,N'-triethylethylenediamine, N,N-dimethyl-N'-ethylethylenediamine, N,N-diethyl-N'-methylethylenediamine, N-propylethylenediamine, N-methyl-1,3-propanediamine, N,N-dimethyl-1,3-propanediamine, N,N'-dimethyl-1,3-propanediamine, N,N-diethyl-1,3-propanediamine, N,N'-diethyl-1,3-propanediamine, N,N-dibutyl-1,3-propanediamine, N,N,N'-trimethyl-1,3-propanediamine, piperazine, N-methylpiperazine, 2-methylpiperazine, 1-(2-aminoethyl)piperidine, 4-(2-aminoethyl)morpholine, 1-(2-aminoethyl)pyrrolidine, 1-(2-aminoethyl)piperazine, 2-(2-aminoethyl)pyridine, 4-(3-aminopropyl)morpholine, 1-(3-aminopropyl)pipecoline, phenylenediamine, acetaldehyde ammonia and 1,3-di-(4-piperidyl)propane.

7. A process according to claim 1, wherein the secondary amine compound is selected from the group consisting of diethylamine, piperidine, pyrolidine, piperazine and morpholine.

8. A process according to claim 1, wherein the fluoroolefin is trifluoroethylene, tetrafluoroethylene, hexafluoropropene, octafluoroisobutene or chlorotrifluoroethylene.

9. A process according to claim 1, wherein the fluoroolefin is tetrafluoroethylene.

10. A process according to claim 8, wherein the fluoroolefin is tetrafluoroethylene.

* * * * *